(12) United States Patent
Jayne et al.

(10) Patent No.: US 9,267,869 B2
(45) Date of Patent: Feb. 23, 2016

(54) PARTICLE CAPTURE DEVICE

(71) Applicant: Aerodyne Research, Inc., Billerica, MA (US)

(72) Inventors: John T. Jayne, Littleton, MA (US); Douglas R. Worsnop, Lexington, MA (US)

(73) Assignee: Aerodyne Research, Inc., Billerica, MA (US)

( * ) Notice: Subject to any disclaimer, the term of this patent is extended or adjusted under 35 U.S.C. 154(b) by 354 days.

(21) Appl. No.: 13/961,469

(22) Filed: Aug. 7, 2013

(65) Prior Publication Data

US 2015/0040689 A1 Feb. 12, 2015

(51) Int. Cl.
*G01N 1/22* (2006.01)
*G01N 1/44* (2006.01)
*G01N 1/28* (2006.01)
*G01N 15/02* (2006.01)
(Continued)

(52) U.S. Cl.
CPC ............... *G01N 1/44* (2013.01); *G01N 1/2208* (2013.01); *G01N 1/28* (2013.01); *G01N 15/0255* (2013.01); *G01N 15/0266* (2013.01); *G01N 15/1031* (2013.01); *G01N 2015/0038* (2013.01); *G01N 2015/0046* (2013.01); *G01N 2015/1043* (2013.01)

(58) Field of Classification Search
CPC ............. G01N 1/42; G01N 1/44; G01N 1/22; G01N 1/02; G01N 1/10
USPC ...................................................... 73/863.11
See application file for complete search history.

(56) References Cited

U.S. PATENT DOCUMENTS

| | | | | | |
|---|---|---|---|---|---|
| 2,709,222 | A | * | 5/1955 | Lawrence | B01D 59/48 250/284 |
| 4,589,843 | A | * | 5/1986 | Smith | F23D 14/12 266/102 |
| 4,730,111 | A | * | 3/1988 | Vestal | G01N 30/7253 250/281 |

(Continued)

FOREIGN PATENT DOCUMENTS

DE 3938194 A1 5/1991

OTHER PUBLICATIONS

Jayne, John T., et al., "Development of an Aerosol Mass Spectrometer for Size and Composition Analysis of Submicron Particles," Aerosol Science and Technology, American Association for Aerosol Research, vol. 33, No. 1-2, Jul.-Aug. 2000, pp. 49-70.

(Continued)

*Primary Examiner* — Hezron E Williams
*Assistant Examiner* — Rodney T Frank
(74) *Attorney, Agent, or Firm* — Cesari and McKenna, LLP; James A. Blanchette

(57) ABSTRACT

In example embodiments, particle collection efficiency in aerosol analyzers and other particle measuring instruments is improved by a particle capture device that employs multiple collisions to decrease momentum of particles until the particles are collected (e.g., vaporized or come to rest). The particle collection device includes an aperture through which a focused particle beam enters. A collection enclosure is coupled to the aperture and has one or more internal surfaces against which particles of the focused beam collide. One or more features are employed in the collection enclosure to promote particles to collide multiple times within the enclosure, and thereby be vaporized or come to rest, rather than escape through the aperture.

20 Claims, 6 Drawing Sheets

(51) Int. Cl.
*G01N 15/00* (2006.01)
*G01N 15/10* (2006.01)

(56) References Cited

U.S. PATENT DOCUMENTS

| | | | | |
|---|---|---|---|---|
| 4,814,612 | A * | 3/1989 | Vestal | G01N 30/7253 250/282 |
| 4,968,885 | A | 11/1990 | Willoughby | |
| 5,538,643 | A * | 7/1996 | Kallos | G01N 30/84 210/198.2 |
| 6,040,574 | A | 3/2000 | Jayne et al. | |
| 6,068,978 | A * | 5/2000 | Zaun | B01L 3/502 422/141 |
| 7,247,495 | B2 * | 7/2007 | Amirav | G01N 30/72 250/281 |
| 2012/0255375 | A1 * | 10/2012 | Kwok | G01N 1/2208 73/863.22 |
| 2013/0011930 | A1 | 1/2013 | Takegawa et al. | |

OTHER PUBLICATIONS

Middlebrook, Ann M., et al., "Evaluation of Composition-Dependent Collection Efficiencies for the Aerodyne Aerosol Mass Spectrometer Using Field Data," Aerosol Science and Technology, American Association for Aerosol Research, vol. 46, Aug. 2011, pp. 258-271.

Takegawa, N., et al., "Evaluation of a New Particle Trap in a Laser Desorption Mass Spectrometer for Online Measurement of Aerosol Composition," Aerosol Science and Technology, American Association for Aerosol Research, vol. 46, Sep. 2011, pp. 429-443.

Williams, Brent J., et al., "An In-Situ Instrument for Speciated Organic Composition of Atmospheric Aerosols: Thermal Desorption Aerosol GC/MS-FID (TAG)," Aerosol Science and Technology, American Association for Aerosol Research, vol. 40, Apr. 13, 2006, pp. 627-638.

"Notification of Transmittal of the International Search Report and the Written Opinion of the International Searching Authority, or the Declaration," International Filing Date: Jul. 14, 2014, International Application No. PCT/US2014/046508, Applicant: Aerodyne Research, Inc., Date of Mailing: Oct. 23, 2014, pp. 1-11.

* cited by examiner

DETAIL K

PARTICLE CAPTURE DEVICE

GOVERNMENT LICENSE RIGHTS

This invention was made with government support under Contract No. DE-SC0001673 awarded by the Department of Energy. The Government has certain rights in this invention.

BACKGROUND

1. Technical Field

The present disclosure relates generally to aerosol analyzers and other particle measuring instruments, and more specifically to a particle capture device usable in aerosol analyzers and other particle measuring instruments.

2. Background Information

Fine atmospheric aerosols resulting from internal combustion engines, fossil fuel fired power plants, painting/stripping faculties, gas discharge boiler operations and other anthropogenic and biogenic sources, are known to have a serious impact on climate and human health. These aerosols are comprised of micron and sub micron sized particles, having various size distributions and chemical compositions. Such particles can influence climate directly by scattering or absorbing sunlight, and indirectly by altering cloud coverage. Further, such particles can contribute to health problems such as asthma, lung cancer, cardiovascular disease, respiratory disease, and other conditions. Given their impact on climate and human health, fine atmospheric aerosols composed of micron and sub micron sized particles are the subject to widespread study and monitoring.

A variety of different types of aerosol analyzers and other particle measuring instruments have been developed to determine particle size distributions and chemical compositions of fine atmospheric aerosols. In one type of instrument, a focused particle beam is generated and directed towards a generally flat collection surface. The particles impact the collection surface, and a portion of them are retained. The retained particles are vaporized, and the resulting gaseous molecules are provided to a detector that produces results. While such an instrument may provide valuable information, typical designs have shortcomings.

One shortcoming of typical designs is that they have low particle collection efficiency. A significant percentage of particles impacting the collection surface may simply bounce off (i.e. impact and rebound), and be lost rather than vaporized and analyzed. Low particle collection efficiency may limit the overall performance of the instrument. While attempts have been made to increase particle collection efficiency, such attempts have had mixed results.

Some attempts have focused on changing particle properties to reduce particle bounce. Modifications are made to the particles before they impact the collection surface. Other attempts have focused on modifying the impact surface, such as using greased plate impactors. However, particle bounce is a complex phenomenon. A wide variety of factors, including size, chemical composition, phase (e.g., liquid or solid), impact velocity, and the like, may be in play. Given the complexities, modifying particle or impact surface properties to reduce particle bounce is challenging.

Other attempts have focused on applying corrections to compensate for low particle collection efficiency. Empirically determined correction factors may be applied to results to compensate for losses of mass or losses of concentration resulting from particle bounce. However, determining the appropriate correction factors may be challenging. Further, correction factors merely mask, and do not address, the underlying problem of low particle collection efficiency.

Accordingly, there is a need for improved techniques that may be used to, among other things, improve particle collection efficiency in aerosol analyzers and other particle measuring instruments.

SUMMARY

In example embodiments, particle collection efficiency in aerosol analyzers and other particle measuring instruments is improved by a particle capture device that employs multiple collisions to decrease momentum of particles until the particles are collected (e.g., vaporized or come to rest). The particle collection device includes an aperture through which a focused particle beam enters. A collection enclosure is coupled to the aperture and has one or more internal surfaces against which particles of the focused beam collide. One or more features are employed with the internal surfaces to promote particles to collide multiple times within the enclosure, and thereby be vaporized or come to rest, rather than escape through the aperture.

To promote multiple collisions, a ratio of an internal collision area of the collection enclosure to an entrance area of the aperture may be maximized. A surface area of the internal surfaces of the collection enclosure defines the internal collision area. Boundaries of the aperture define the entrance area. The ratio should be greater than 1:1, and preferable should be greater than 20:1. In one implementation, the ratio is approximately 37:1. The ratio may be maximized by utilizing a special geometry for the internal surfaces of the collection enclosure. The ratio may also be maximized by altering surface properties of the internal surfaces of the collection enclosure. Further, a combination of the two approaches may be employed.

It should be understood that a variety of additional features and alternatives may be implemented. This Summary is intended simply as a brief introduction to the reader, and does not indicate or imply that the examples mentioned herein cover all aspects of the invention, or are necessary or essential aspects of the invention.

BRIEF DESCRIPTION OF THE DRAWINGS

The description below refers to the accompanying drawings of example embodiments, of which.

DETAILED DESCRIPTION OF AN EXAMPLE EMBODIMENTS

Figure 1:
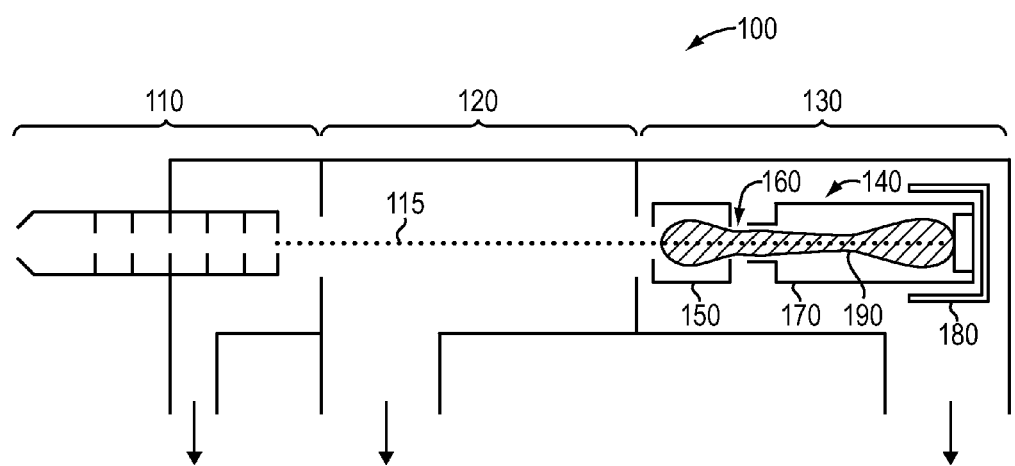
FIG. 1 is a schematic diagram of an example aerosol analyzer in which an example particular capture device may be employed.
Figure 2:
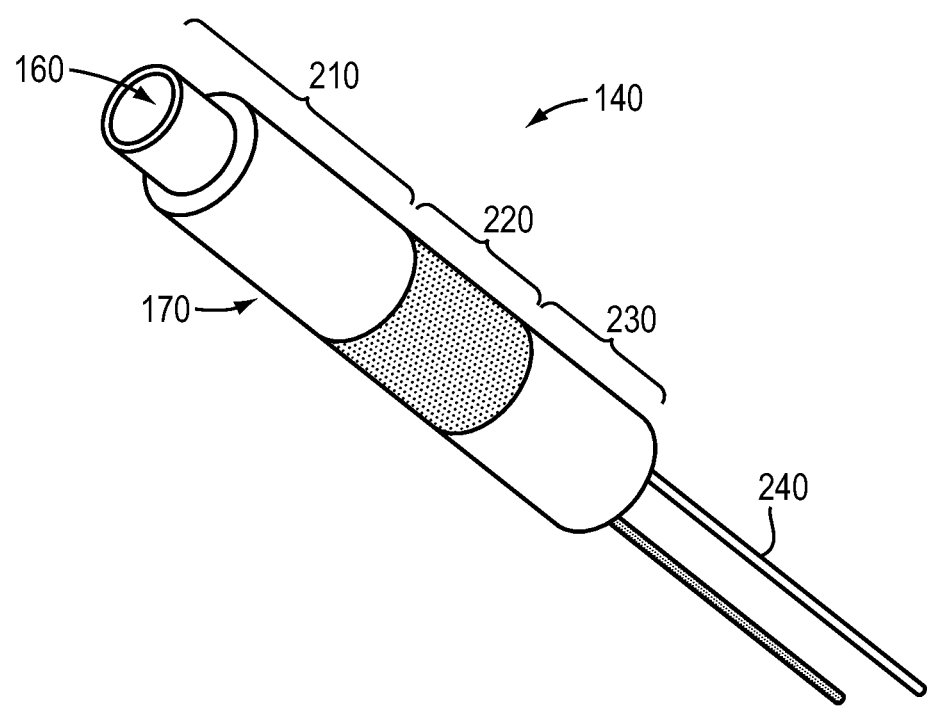
FIG. 2 is a perspective view of an example particle capture device that utilizes geometry to promote multiple collisions.

Referring to FIG. 1, an example aerosol analyzer 100 may include three main sections: an aerosol sampling chamber 110, a particle sizing chamber 120, and a particle composition detection chamber 130. The aerosol sampling chamber 110 draws in particle-laden gas (e.g., atmospheric air) having micron and/or sub-micron particles, and produces a focused particle beam 115. In one implementation, the aerosol sampling chamber 110 includes a series of orifice lenses under the pull of a vacuum system. The lenses serve to focus particles and to control supersonic gas expansion and particle acceleration, to form the focused particle beam 115. The focused particle beam 115 is passed to the particle sizing chamber 120. In the particle sizing chamber, particles are separated according to their size dependant velocity profile resulting from expansion into vacuum. In one configuration, the particle sizing chamber 120 includes a particle changing unit (not shown) that applies an electric charge to the particles, and a deflection section (not shown) where an electric field deflects the particles. The degree of deflection is related to particle size (size dependant velocity, size dependant charge and applied voltage). Particles within a narrow range of sizes are caused to pass through an off-axis slit and leave the particle sizing chamber and pass into the particle composition detection chamber 130. In another configuration, the particle sizing chamber 120 includes a beam chopper (not shown) that alternately blocks and passes the focused particle beam 115 to produce a succession of beam pulses. Particles undergo velocity dispersion where the velocities are inversely related to particle size. Accordingly, as each beam pulse travels, it spreads in the direction of travel, with smaller particles arriving before larger particles. Particles of sorted sizes are thereby be delivered to the particle composition detection chamber 130.

The particle detection chamber 130 includes a particular capture device 140 and a detector 150. The focused particle beam enters the particle capture device 140 through an aperture 160. The focused particle beam 115 is then received into a collection enclosure 170 coupled to the aperture 160. A temperature change element 180 of the particular capture device 140 is arranged to heat and/or cool the collection enclosure 170, depending on the implementation. The temperature change element 180 may include a resistive heating element, a thermo eclectic cooling element (e.g., a Peltier cooler), a heating or cooling system that circulates hot or cold liquid through a closed loop circulation system, an irradiation heating source, such as a $CO_2$ laser, or another type of element that is capable of changing the temperature of the enclosure 170.

Particles are substantially retained in the collection enclosure 170 of the particular capture device 140 until they are vaporized (e.g., as a result of heat from the temperature change element 180), or come to rest (e.g., for later vaporization in a controlled heating cycle). In general, the particle capture device 140 may operate as a particle capture vaporizer or as a particle capture collector, depending on the implementation. In an implementation where the particular capture device 140 operates as a particle capture vaporizer, the temperature change element 180 may continuously heat the collection enclosure 170 to vaporize collected particles substantially immediately (i.e., as soon as possible). In an implementation where the particular capture device 140 operates as a particle capture collector, the temperature change element 180 may perform controlled heating cycles, with periods of heat interspersed by periods of relative cool. Entering particles may encounter an initially cool collection enclosure 170, such that collected particles are not immediately vaporized. The collected particles may later be subjected to heating and be vaporized. The heating cycle may be precisely controlled to allow particle volatility to be studied providing further information on particle composition.

Vaporized particles 190 are passed to the detector 150, which may be a mass spectrometer. In one implementation, the vaporized particles pass to the detector through the same aperture 160 that the focused particle beam originally entered. That is, the vaporized particles 190 exit the particular capture device 140 along the same axis upon which they entered as a focused particle beam 115. The aperture 160 is located within a detection region of the detector 150. In an implementation where the detector 150 includes a mass spectrometer, the aperture is within an ion formation chamber of the mass spectrometer.

As discussed above, previous collection surfaces have suffered from low particle collection efficiency. A significant percentage of particle simply bounce off the collection surfaces to be lost, such that they are not vaporized or collected for later vaporization. Rather than attempt to eliminate particle bounce, the particle capture device 140 assumes particles will bounce, and employs multiple collisions to decrease the momentum of particles until they are collected (e.g., vaporized or come to rest). The collection enclosure 170 of the particle capture device 140 includes one more internal surfaces upon which the particles collide multiple times. A surface area of the internal surfaces defines an internal collision area. Boundaries of the aperture 160 of the particle capture device 140 define an entrance area. To provide for particles to be collected, rather than lost, a ratio of the internal collision area to the entrance area (referred to herein as the "capture efficiency ratio") is maximized within practical constraints. The capture efficiency ratio should be greater than 1:1, and preferable should be greater than 20:1. In one implementation, the capture efficiency ratio is approximately 37:1.

The capture efficiency ratio may be increased somewhat by reducing the entrance area. The minimum size of the aperture 160 may be defined by the width of the focused particle beam to allow full entrance thereof. The capture efficiency ratio may be increased more significantly by maximizing the internal collision area. The internal collision area may be maximized through geometry of the internal surfaces of the collection enclosure 170 and/or through surface properties of the internal surfaces of the collection enclosure 170. Geometry may be used where specular reflections dominate. With substantially smooth internal surfaces, particles may bounce in a relatively predictable manner through specular reflection. Geometry of the internal surfaces can increase specular reflections, such that particles repeatedly collide with the internal surfaces until they are vaporized or come to rest.

Referring to the FIGS. 2-5, an example geometry is shown that promotes multiple collisions. In this example, the particle capture device 140 has a generally cylindrical configuration, and is largely symmetrical about its major axis J-J. A front portion 210 of the particle capture device 140 includes the aperture 160 and the collection enclosure 170. The front portion 210 may be constructed from a solid piece of material, for example, a refractory metal such as Molybdenum or Tungsten. A heater body portion 220 of the particle capture device 140 functions as the temperature change element, in this case, providing resistive heating as current is applied to wires 240. The heater body portion 220 may be constructed from a solid piece of material also, for example, Molybdenum or Tungsten. A thermal support portion 230 of the particle capture device 140 is a thin walled tube connected to the heater body 220 and encloses part of the wires 240. By applying either continuous or cyclic heating, the particle capture device 140 may function as a particle capture vaporizer or as a particle capture collector, as discussed above. An embedded thermocouple (not shown) inside heater body 220 or at the front of heater body 220 allows for temperature measurement.

Figure 3:
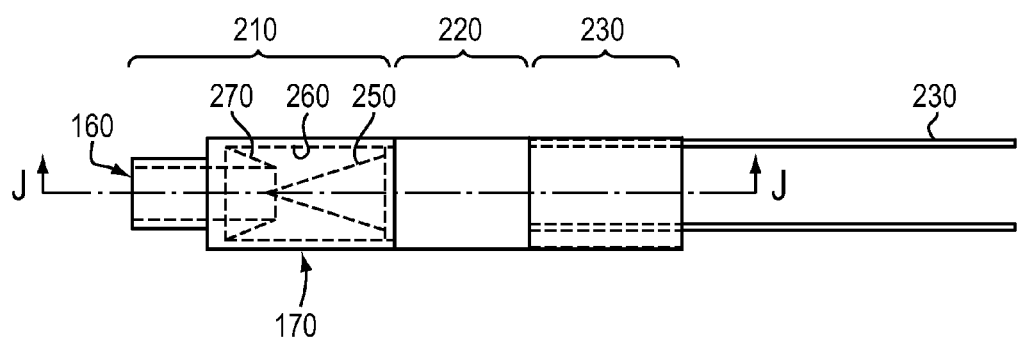
FIG. 3 is a first cross section of the example particle capture device of FIG. 2.
Figure 4:
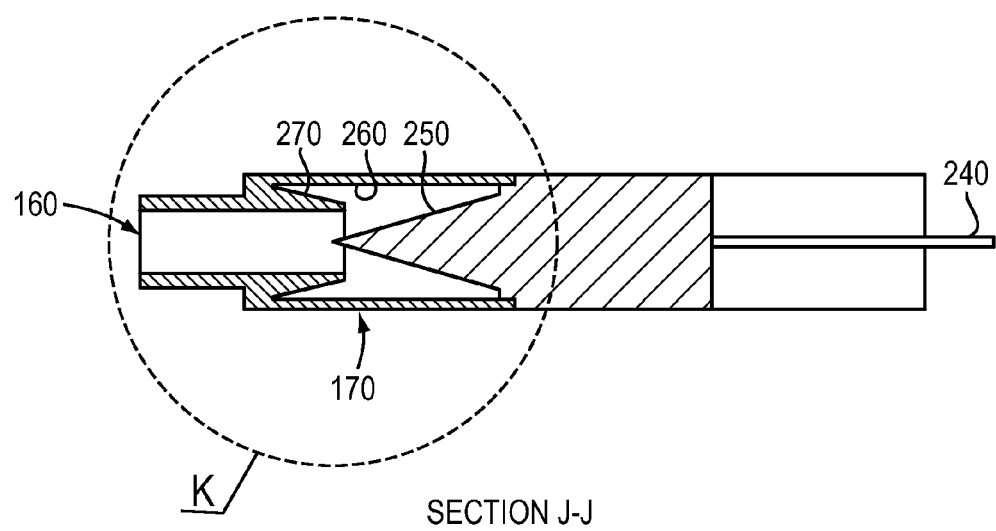
FIG. 4 is a second cross section of the example particle capture device of FIGS. 2 and 3, taken along major axis J-J in FIG. 3.
Figure 5:
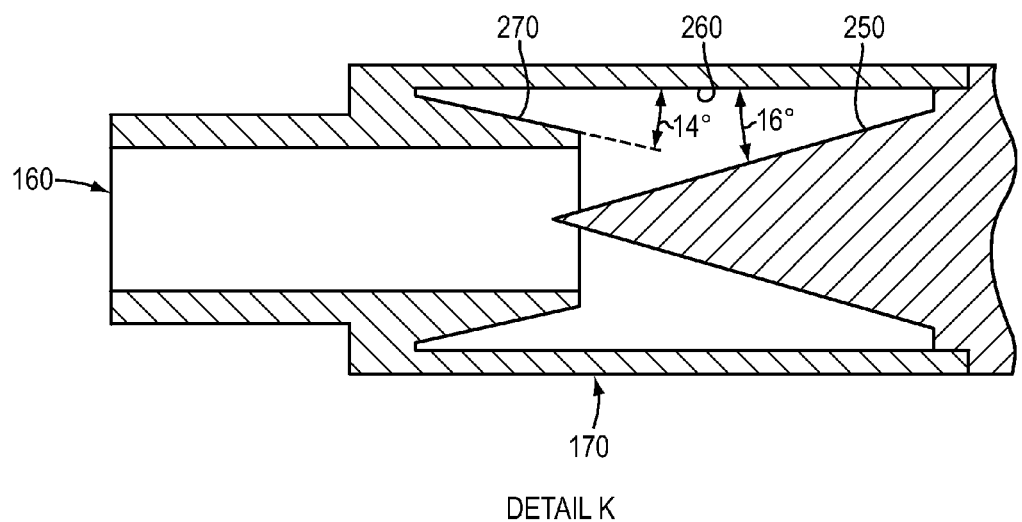
FIG. 5 is an enlarged cross section of the example particle capture device of FIGS. 2-4, showing detail of region K in FIG. 4.

A focused particle beam may enter the aperture 160 and be received into the collection enclosure 170. The collection enclosure 170, as shown in FIGS. 3-5, includes several substantially smooth internal surfaces 250, 260, 270 upon which the particles of the focused particle beam collide, and a portion thereof bounce (e.g., rebound). The internal surfaces 250, 260, 270 are arranged to promote multiple collisions and minimize the possibility of particles escaping through the aperture 160, before the particles are vaporized or come to rest, as the case may be. The geometry may serve to substantially equally distribute the particles to all points on the internal surfaces 250, 260, 270, in a manner similar to an integrating sphere in the field of optics, which distributes light over all angles.

In the depicted example, a first internal surface 250 is positioned to receive the initial collision of the particles. The first internal surface 250 is oriented at an acute angle to the major axis J-J of the particle capture device 140 (and thereby at an acute angle to the trajectory of the focused particle beam), such that initial collisions (assuming spectral reflection) reduce momentum of the particles, but preserve the direction of the forward velocity vector components of the particles. That is, the orientation causes the particles to bounce (assuming spectral reflection) further into the collection enclosure 170 rather than towards that aperture 160. Preferably the angle between the major axis J-J (and the particle beam trajectory) and the first internal surface 250 is less than 30°. A shallower angle may lead to a more efficient but larger particle capture device 140. In one implementation, the angle between the major axis J-J (and the particle beam trajectory) and the first surface 250 is 16°. The first surface 250 may have a substantially conical shape, with a vertex angle of 16°.

The second internal surface 260 is oriented at an acute angle to the first internal surface 250 and is configured to receive the next collision (assuming spectral reflection). The orientation again causes the particles to bounce (assuming spectral reflection) further into the collection enclosure 170 rather than towards that aperture 160. In one implementation, the second internal surface 260 is parallel to the major axis J-J such that an angle between the second internal surface 260 and the first internal surface is again 16°. The second internal surface 260 may have a substantially cylindrical shape.

Particles may repeatedly bounce between the first internal surface 250 and the second internal surface 260 and may eventually encounter the third internal surface 270. The third internal surface 270 is oriented at an acute angle with respect to the second internal surface 260, and is configured to retain particles that are moving in a direction towards the aperture 160. In one implementation, an angle between the second internal surface 260 and the third internal surface is 270 is 14°. The third internal surface 270 may be shaped sustainably as a conical frustum, with the aperture 160 at its apex.

Figure 6:
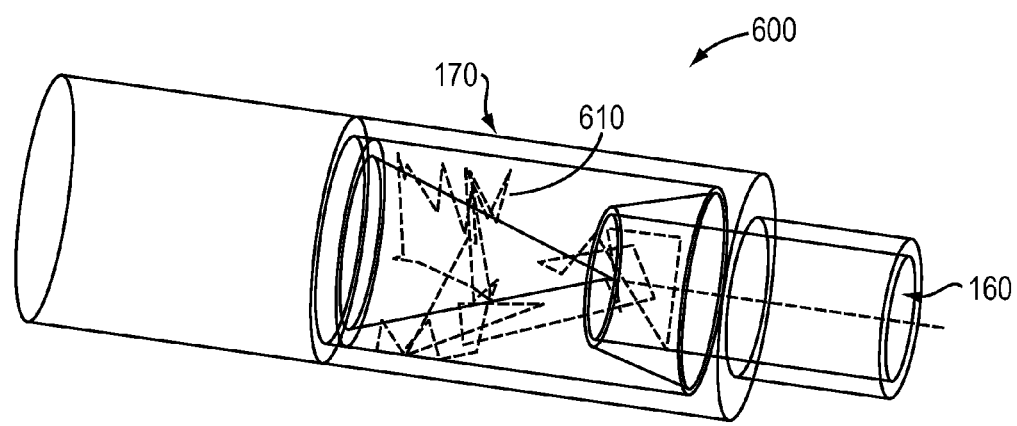
FIG. 6 is a ray trace model of an example single particle trajectory in the example particle capture device of FIGS. 2-5.

It should be understood that spectral reflection is an idealized case, and even with substantially smooth surfaces, particles exhibit some variation in how they rebound. The example geometry of the example particle capture device 140 may minimize the number of particles that escape despite this variation. Referring to the ray trace model 600 of a single particle trajectory 610 shown in FIG. 6, it can be seen that a particle is likely to undergo multiple collisions after it enters the collection enclosure 170, and finally be vaporized or come to rest.

As mentioned above, rather than, or in addition to special geometry, surface properties of one or more internal surfaces of the collection enclosure 170 may be used to promote multiple collisions. When surface roughness is introduced to one or more internal surfaces, colliding particles may undergo more random reflections such that diffuse reflections dominate. Surface roughness may be introduced by adding wires entanglements (e.g., wire "birds nests"), constructing the surfaces from porous materials (e.g., which provide nooks and crevices), adding micro-scaled or nano-scaled grids produced from nano-technology processes or etching processes, or some other means of adding add surface roughness. Surface roughness and the diffuse reflections resulting therefrom, may be used together with special geometry to improve particle collection efficiency. However, diffuse reflections may also limit particle collection efficiency, and proved unwanted, in some cases.

While the above description discusses various example embodiments of the present disclosure, it should be apparent that a number of modifications and/or additions may be made without departing from the disclosure's intended spirit and scope.

For example, while it is discussed above that the particle device 140 may be used in an example aerosol analyzer 100 designed to measure fine atmospheric aerosols, it should be understood such the device 140 may also be used in a variety of other types of instruments, including other particle measuring instruments that measure particles from non-atmospheric sources. Such particle measuring instruments may lack some of the capabilities of the example aerosol analyzer 100, for instance the ability to produce results as function of particle size, and may have additional capabilities beyond those of the example aerosol analyzer 100.

Further, while certain materials such as Molybdenum and Tungsten, and certain shapes such as cylinders, cones and conical frustums, are discussed above, it should be understood the particle capture device 140 and, specifically the collection enclosure 170, may be constructed from a variety of different materials, and be formed in a variety of different shapes suited for the goals discussed herein. In general, it should be understood that the above descriptions are meant to be taken only by way of example.

What is claimed is:

1. A particle capture device for capturing micron and/or sub-micron sized particles in an instrument, comprising:
    an aperture through which a focused particle beam including micron and/or sub-micron particles enters the particle capture device;
    a collection enclosure coupled to the aperture and into which the focused particle beam is received, the collection enclosure having one or more internal surfaces upon which the particles collide multiple times until the particles are vaporized or come to rest for subsequent vaporization, the one or more internal surfaces including a first internal surface arranged in an initial trajectory of the focused particle beam to receive an initial collision of particles, the first internal surface orientated at an angle with respect to the initial trajectory, the angle sufficient to provide that the initial collision reduces momentum of the particles but preserves a direction of a forward velocity vector component of the particles; and
    a temperature control element configured to heat and/or cool the collection enclosure.

2. The particle capture device of claim 1, wherein an area between boundaries of the aperture defines an entrance area, a surface area of the one or more internal surfaces upon which the particles collide defines an internal collision area, and a ratio of the internal collision area to the entrance area is greater than 20:1.

3. The particle capture device of claim 1, wherein the particle capture device operates as a particle capture vaporizer, and the temperature control element is configured to continuously heat the collection enclosure during operation, wherein the particles collide multiple times until the particles are vaporized.

4. The particle capture device of claim 1, wherein the particle capture device operates as a particle capture collector, the temperature control element is configured to heat the collection enclosure in controlled heating cycles,
wherein the particles collide multiple times until the particles come to rest.

5. The particle capture device of claim 1, wherein the aperture is both an entrance and exit aperture, such that the focused particle beam enters the collection enclosure and the vaporized particles exit the collection enclosure through the same aperture.

6. The particle capture device of claim 1, wherein the one or more internal surfaces are each substantially smooth surfaces.

7. The particle capture device of claim 1, wherein the one or more internal surfaces are a plurality of internal surfaces arranged in a geometry that promotes multiple collisions.

8. The particle capture device of claim 7, wherein the geometry substantially equally distributes particles to all points over the plurality of internal surfaces.

9. The particle capture device of claim 1, wherein the angle is an acute angle with respect to the initial trajectory, the acute angle being less than 30°.

10. The particle capture device of claim 7, wherein the geometry comprises:
the first internal surface oriented at a first acute angle with respect to the initial trajectory;
a second internal surface oriented at a second acute angle with respect to the first internal surface; and
a third internal surface oriented at a third acute angle with respect to the second surface.

11. The particle capture device of claim 10, wherein the first and second acute angles are 16° and the third acute angle is 14°.

12. The particle capture device of claim 1, wherein the one or more internal surfaces are each roughened surfaces.

13. The particle capture device of claim 12, wherein the one or more internal surfaces include one or more of: wire entanglements, pores, or grids.

14. A particle capture device for capturing micron and/or sub-micron sized particles in an instrument, comprising:
an aperture through which a focused particle beam including micron and/or sub-micron particles enters the particle capture device;
a collection enclosure coupled to the aperture and into which the focused particle beam is received, the collection enclosure having a plurality of internal surfaces arranged in a geometry that causes particles to collide multiple times until the particles are vaporized or come to rest for subsequent vaporization, the geometry including a first internal surface arranged in an initial trajectory of the focused particle beam to receive an initial collision of particles, the first internal surface orientated at a first acute angle with respect to the initial trajectory, the first acute angle being less than 30°; and
a temperature control element configured to heat and/or cool the collection enclosure.

15. The particle capture device of claim 14, wherein the particle capture device operates as a particle capture vaporizer, and the temperature control element is configured to continuously heat the collection enclosure during operation.

16. The particle capture device of claim 14, wherein the particle capture device operates as a particle capture vaporizer, and the temperature control element is configured to heat the collection enclosure in controlled heating cycles.

17. The particle capture device of claim 14, wherein the aperture is both an entrance and exit aperture, such that the focused particle beam enters the collection enclosure and the vaporized particles exit the collection enclosure through the same aperture.

18. The particle capture device of claim 14, wherein the geometry further comprises
a second internal surface oriented at a second acute angle with respect to the first internal surface; and
a third internal surface oriented at a third acute angle with respect to the second surface.

19. A method for capturing micron and/or sub-micron sized particles in an instrument, comprising:
passing a focused particle beam including micron and/or sub-micron particles through an aperture into a collection enclosure of a particle capture device;
causing the particles to collide multiple times with internal surfaces of the collection enclosure, a first collision of a particle to be against a first internal surface of the collection enclosure, the first collision to reduce momentum of the particle but preserve a direction of a forward velocity vector component of the particle; and
heating the collection enclosure to vaporize the particles.

20. The method of claim 19, further comprising:
removing vaporized particles from the collection enclosure through the same aperture that the focused particle beam entered the collection enclosure.

* * * * *